US010751367B2

(12) United States Patent
Deng et al.

(10) Patent No.: US 10,751,367 B2
(45) Date of Patent: *Aug. 25, 2020

(54) BIOACTIVE GLASS MICROSPHERES (71) Applicant: Corning Incorporated, Corning, NY (US)

(72) Inventors: Huayun Deng, Painted Post, NY (US); Ye Fang, Painted Post, NY (US); Qiang Fu, Painted Post, NY (US); Lina Ma, Corning, NY (US); John Christopher Mauro, Corning, NY (US); Michael Joshua Snyder, Almond, NY (US); Dana Lynne Widmer-Quiel, Horseheads, NY (US)

(73) Assignee: Corning Incorporated, Corning, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/603,208

(22) Filed: May 23, 2017

(65) Prior Publication Data

US 2017/0340666 A1  Nov. 30, 2017

Related U.S. Application Data (60) Provisional application No. 62/342,411, filed on May 27, 2016.

(51) Int. Cl.
*A61K 33/42* (2006.01)
*C03C 3/19* (2006.01)
*C03B 19/10* (2006.01)
*C03C 11/00* (2006.01)
*C03C 3/064* (2006.01)
*C03C 12/00* (2006.01)
*C03C 4/00* (2006.01)
*A61L 26/00* (2006.01)
*A61L 15/18* (2006.01)
*A61L 15/44* (2006.01)

(52) U.S. Cl.
CPC .............. *A61K 33/42* (2013.01); *A61L 15/18* (2013.01); *A61L 15/44* (2013.01); *A61L 26/0004* (2013.01); *A61L 26/0066* (2013.01); *C03B 19/102* (2013.01); *C03C 3/064* (2013.01); *C03C 3/19* (2013.01); *C03C 4/0007* (2013.01); *C03C 4/0014* (2013.01); *C03C 11/002* (2013.01); *C03C 12/00* (2013.01)

(58) Field of Classification Search
None
See application file for complete search history.

(56) References Cited

U.S. PATENT DOCUMENTS

| | | |
|---|---|---|
| 2,532,386 A | 12/1950 | Armistead |
| 2,978,339 A | 4/1961 | Veatch et al. |
| 3,323,888 A | 6/1967 | Searight et al. |
| 3,778,335 A | 12/1973 | Boyd |
| 3,790,430 A | 2/1974 | Mochel |
| 4,083,727 A | 4/1978 | Andrus et al. |
| 4,084,972 A | 4/1978 | Andrus et al. |
| 4,126,437 A | 11/1978 | O'Horo |
| 4,140,645 A | 2/1979 | Beall et al. |
| 4,233,169 A | 11/1980 | Beall et al. |
| 4,323,056 A | 4/1982 | Borrelli et al. |
| 4,340,693 A | 7/1982 | Drake |
| 4,889,707 A | 12/1989 | Day |
| 5,081,394 A | 1/1992 | Morishita et al. |
| 5,153,070 A | 10/1992 | Andrus |
| 5,648,124 A | 7/1997 | Sutor |
| 5,674,790 A | 10/1997 | Araujo |
| 5,849,816 A | 12/1998 | Suskind et al. |
| 5,876,452 A | 3/1999 | Athanasiou et al. |
| 6,214,471 B1 | 4/2001 | Beall |
| 6,254,981 B1 | 7/2001 | Castle |
| 6,280,863 B1 | 8/2001 | Frank et al. |
| 6,328,990 B1 | 12/2001 | Ducheyne et al. |
| 6,338,751 B1 | 1/2002 | Litkowski et al. |
| 6,506,399 B2 | 1/2003 | Donovan |
| 6,514,892 B1 | 2/2003 | Kasai et al. |
| 6,802,894 B2 | 10/2004 | Brodkin |
| 6,838,171 B2 | 1/2005 | Nomura |
| 6,852,656 B1 * | 2/2005 | La Greca ............... C03C 13/00 501/35 |
| 7,166,548 B2 | 1/2007 | Apel et al. |
| 7,166,549 B2 | 1/2007 | Fechner et al. |
| 7,597,900 B2 | 10/2009 | Zimmer et al. |
| 7,704,903 B2 | 4/2010 | Seneschal et al. |

(Continued)

FOREIGN PATENT DOCUMENTS

| | | |
|---|---|---|
| CA | 2577628 C | 11/2010 |
| CA | 2926665 A1 | 5/2015 |

(Continued)

OTHER PUBLICATIONS

El-Kheshen et al. Ceramics Int. (2008) 34: 1667-1673 (Year: 2008).*
Fu et al. J. Biomed. Res. (2010) 95A(1): 164-171 (Year: 2010).*
Andersson et al. J. Mat. Sci: Materials in Medicine (1990) 1:219-227 (Year: 1990).*
Hench J. Am. Cermaic Sci. (1998) 81(7): 1705-1728 (Year: 1998).*
Bertling, et al., "Hollow microspheres". Chem Eng Technol, 2004, 27: 829-837.
Fu, H., et al., "Hollow hydroxyapatite microspheres as a device for controlled delivery of proteins". J Mater Sci: Mater Med., 2011;22:579-91.
V. V. Budov, "Hollow glass microspheres. Use, properties and technology (review article)", Glass Ceram, 1994, 51: 230-235.
International Search Report and Written Opinion PCT/US2017/034409 dated Oct. 4, 2017.

(Continued)

Primary Examiner — Susan M Hanley (57) ABSTRACT

An aluminoborate composition, an alumino-borosilicate glass composition, or a mixture thereof, and solid or hollow microspheres thereof, as defined herein. Also disclosed are methods of making and using the disclosed compositions, for example, forming microspheres for use in bioactive applications, and composition extracts for use in treating or healing wounds.

19 Claims, 6 Drawing Sheets

(56) References Cited

U.S. PATENT DOCUMENTS

| | | | |
|---|---|---|---|
| 7,709,027 B2 | 5/2010 | Fechner et al. | |
| 7,905,115 B2 | 3/2011 | Rake et al. | |
| 7,989,065 B2 | 8/2011 | Winstead | |
| 8,080,490 B2 | 12/2011 | Fechner et al. | |
| 8,173,154 B2 * | 5/2012 | Jung | A61F 13/00008 |
| | | | 424/445 |
| 8,637,300 B2 | 1/2014 | Ruf et al. | |
| 9,056,045 B2 | 6/2015 | Hughes | |
| 9,084,844 B2 | 7/2015 | Vallittu | |
| 9,168,272 B2 | 10/2015 | Hill et al. | |
| 9,241,879 B2 | 1/2016 | Castillo | |
| 9,326,995 B2 | 5/2016 | Stucky et al. | |
| 9,498,459 B2 | 11/2016 | Pomrink et al. | |
| 9,622,483 B2 | 4/2017 | Bookbinder et al. | |
| 9,688,567 B2 | 6/2017 | Rampf et al. | |
| 9,701,573 B2 | 7/2017 | Beall et al. | |
| 2004/0120908 A1 | 6/2004 | Cohen et al. | |
| 2004/0228905 A1 | 11/2004 | Greenspan et al. | |
| 2005/0118236 A1 | 6/2005 | Qiu et al. | |
| 2005/0142077 A1 | 6/2005 | Zimmer et al. | |
| 2005/0158395 A1 | 7/2005 | Zimmermann et al. | |
| 2006/0127427 A1 | 6/2006 | Vernice et al. | |
| 2006/0292280 A1 | 12/2006 | Soper et al. | |
| 2007/0122356 A1 | 5/2007 | Kessler et al. | |
| 2008/0214428 A1 | 9/2008 | Orlich et al. | |
| 2008/0233201 A1 | 9/2008 | Royere | |
| 2009/0208428 A1 | 8/2009 | Hill | |
| 2011/0008293 A1 | 1/2011 | Bhandari | |
| 2011/0009254 A1 | 1/2011 | Schweiger et al. | |
| 2011/0152057 A1 | 6/2011 | Qi | |
| 2012/0020898 A1 | 1/2012 | Mandadi et al. | |
| 2012/0135848 A1 | 5/2012 | Beall et al. | |
| 2012/0317735 A1 | 12/2012 | Gonzales | |
| 2012/0321567 A1 | 12/2012 | Gonzales | |
| 2013/0266625 A1 | 10/2013 | Benita | |
| 2014/0000891 A1 | 1/2014 | Mahoney et al. | |
| 2014/0026916 A1 | 1/2014 | Havens | |
| 2014/0186274 A1 | 7/2014 | Hodgkinson | |
| 2014/0193499 A1 | 7/2014 | Da Fonte Ferreira | |
| 2014/0212469 A1 | 7/2014 | Rahaman | |
| 2014/0219941 A1 | 8/2014 | Takekawa et al. | |
| 2014/0271913 A1 | 9/2014 | Pomrink et al. | |
| 2014/0349831 A1 | 11/2014 | Cornejo et al. | |
| 2014/0370464 A1 | 12/2014 | Kounga et al. | |
| 2015/0087493 A1 | 3/2015 | Ritzberger | |
| 2015/0104655 A1 | 4/2015 | Kim et al. | |
| 2015/0231042 A1 | 8/2015 | Gonzales | |
| 2015/0239772 A1 | 8/2015 | Baker | |
| 2015/0265509 A1 | 9/2015 | Zhang et al. | |
| 2015/0299031 A1 | 10/2015 | Ritzberger et al. | |
| 2015/0374589 A1 | 12/2015 | Rampf et al. | |
| 2016/0102010 A1 | 4/2016 | Beall et al. | |
| 2016/0145567 A1 | 5/2016 | Henry et al. | |
| 2016/0340239 A1 | 11/2016 | Propster et al. | |
| 2017/0086877 A1 | 3/2017 | Moffarah et al. | |
| 2017/0274118 A1 | 9/2017 | Nazhat et al. | |
| 2017/0340527 A1 | 11/2017 | Chang et al. | |
| 2017/0340666 A1 | 11/2017 | Deng et al. | |
| 2017/0341975 A1 | 11/2017 | Gross et al. | |
| 2017/0342382 A1 | 11/2017 | Deng et al. | |
| 2017/0342383 A1 | 11/2017 | Deng et al. | |
| 2017/0349876 A1 | 12/2017 | Deng et al. | |
| 2017/0354755 A1 * | 12/2017 | Weinberger | C09C 1/28 |
| 2018/0343255 A1 | 11/2018 | Thibadeau, Sr. et al. | |
| 2019/0060523 A1 | 2/2019 | Bakry | |

FOREIGN PATENT DOCUMENTS

| | | |
|---|---|---|
| EP | 0583791 A1 | 2/1994 |
| EP | 935526 A1 | 8/1999 |
| EP | 1452496 A1 | 9/2004 |
| EP | 1021148 B1 | 5/2008 |
| HU | 200302501 B1 | 1/2006 |
| HU | 227595 B1 | 9/2011 |
| JP | 2004359754 A | 12/2004 |
| JP | 2007001846 A | 1/2007 |
| JP | 2007039269 A | 2/2007 |
| KR | 200781952 | 8/2007 |
| KR | 20130112422 A | 10/2013 |
| WO | 1991012032 A1 | 8/1991 |
| WO | 1997018171 A1 | 5/1997 |
| WO | 9727148 A1 | 7/1997 |
| WO | 1998015263 A2 | 4/1998 |
| WO | 1999062835 A1 | 12/1999 |
| WO | 2007141978 A1 | 12/2007 |
| WO | 2008000888 A2 | 1/2008 |
| WO | 2011141896 A1 | 11/2011 |
| WO | 2012137158 | 10/2012 |
| WO | 2014095198 A1 | 6/2014 |
| WO | 2014159240 A1 | 10/2014 |
| WO | 2015034860 | 3/2015 |
| WO | 2015123049 A1 | 8/2015 |
| WO | 2015200017 A1 | 12/2015 |

OTHER PUBLICATIONS

SP16-134 International Searching Authority Invitation to Pay Additional Fees Partial Search Report PCT/US2017/034409 dated Aug. 7, 2017.

L. Hench et al., "Third-Generation Biomedical Materials", Science, vol. 295, Feb. 8, 2002, p. 1016-1017, www.sciencemag.org, Downloaded from www.sciencemag.org on Aug. 5, 2015.

L.L.Hench, "Bioceramics", J. Am. Ceram. Soc., 81, (7), 1705-1728 (1998).

T. Kokubo et al., "How useful is SBF in predicting in vivo bone bioactivity?", Biomaterials, 27, (2006), 2907-2915.

Qiang Fu et al., "Bioactive glass scaffolds for bone tissue engineering: state of the art and future perspectives", Materials Science and Engineering, C 31, (2011), 1245-1256.

L. Peddi et al., "Bioactive borate glass coatings for titanium alloys", J. Mater. Sci: Mater. Med., (2008), 19, p. 3145-3152.

Mohamed N. Rahaman et al., "Bioactive glass in tissue engineering", Acta Biomaterialia, 7, (2011), 2355-2373.

WO2012137158 machine translation, published Oct. 11, 2012.

Dutra Zanotto, "A bright future for glass-ceramics", American Ceramic Society Bulletin, vol. 89, No. 8, pp. 19-27, 2010.

American Type Culture Collection, Product Sheet MC3T3E1, Subclone 14, (ATCC® CRL2594™), p. 1-3, Aug. 2014.

Maziar Montazerian, et al. "History and trends of bioactive glass-ceramics", Journal of Biomedical Materials Research A, 2016, vol. 104A, 1231-1249, 2016 Wiley Periodicals, Inc.

Apel et al., "Influence of ZrO2 on the crystallization and properties of lithium disilicate glass-ceramics derived from a multi-component system", J Eur Ceram Soc, 2007, 27:1571-1577.

Antonio Tilocca et al., "Structural Effects of Phosphorus Inclusion in Bioactive Silicate Glasses", J. Phys. Chem. B 2007, 111, 14256-14264.

K. Franks et al., "The effect of MgO on the solubility behaviour and cell proliferation in a quaternary soluble phosphate baed glass system", J. of Mate. Sciemce: Materials in Medicine, 13, (2002), 549-556.

I. Ahmed et al., "Processing, characterisation and biocompatibility of iron-phosphate glass fibres for tissue engineering", Biomaterials, 25, (2004), 3223-3232.

Huipin Yuan, et al., "Osteoinduction by calciumphosphate biomaterials", Journal of Materials Science: Materials in Medicine 9 (1998) 723-726.

Jianxi Lu, et al., The Biodegradation Mechanism of Calcium Phosphate Biomaterials in Bone, Journal of Biomedical Materials Research, Aug. 2002, 63(4): 408-412.

B.C. Bunker, et al., Phosphate Glass Dissolution in Aqueous Solutions, Journal of Non-Crystalline Solids 64 (1984) 291-316.

Jonathan C. Knowles, Phosphate based glasses for biomedical applications, J. Mater. Chem., 2003, 13, 2395-2401.

Motohiro Uo et al., Properties and cytotoxicity of water soluble Na2O—CaO—P2O5 glasses, Biomaterials, 19, (1998), 2277-2284.

(56) References Cited

OTHER PUBLICATIONS

F. Jay Murray, Issues in Boron Risk Assessment: Pivotal Study, Uncertainty Factors, and ADIs, The Journal of Trace Elements in Experimental Medicine 9, No. 4 (1996):231-243.
R.F. Brown, et al., "Effect of borate glass composition on its conversion to hydroxyapatite and on the proliferation of MC3T3-E1 cells." Journal of Biomedical Materials Research Part A, 88, No. 2, (2009): 392-400.
A. Saranti, et al., "Bioactive glasses in the system CaO—B2O3—P2O5; preparation, structural study and in vitro evaluation." Journal of Non-Crystalline Solids 352, No. 5 (2006): 390-398.
L. Hench, and J. Jones, eds. Biomaterials, artificial organs and tissue engineering. Elsevier, 2005—book.
E.A. Abou Neel, et al., "Effect of iron on the surface, degradation and ion release properties of phosphate-based glass fibres." Acta Biomaterialia 1, No. 5 (2005): 553-563.
E.A. Abou Neel, et al., "Characterisation of antibacterial copper releasing degradable phosphate glass fibres.", Biomaterials 26, No. 15 (2005): 2247-2254.
C. M. Rochman, et al., Scientific evidence supports a ban on microbeads, Environ Sci & Tech, 2015, 49: 10759-10761.
Wei Xiao et al., "Hollow hydroxyapatite microspheres: a novel bioactive and osteoconductive carrier for controlled release of bone morphogenetic protein-2 in bone regeneration", Acta Biomater. Sep. 2013 ; 9(9): 8374-8383.
Wanpeng Cao et al., Bioactive Materials, Ceramics International, 22, (1996) 493-507.
Fabienne C. Raszewski et al., Methods for Producing Hollow Glass Microspheres, Savannah River National Laboratory, Aiken, SC 29808, Mar. 2016.
Imogen E. Napper et al., Characterisation, quantity and sorptive properties of microplastics extracted from cosmetics, Marine Pollution Bulletin, vol. 99, Issues 1-2, Oct. 15, 2015, pp. 178-185.
Alexis J. de Kerchove et al., Formation of Polysaccharide Gel Layers in the Presence of Ca2+ and K+ Ions: Measurements and Mechanisms, Biomacromolecules, 2007, 8, 113-121.
Marianne Hiorth et al., Immersion coating of pellets with calcium pectinate and chitosan, International Journal of Pharmaceutics 308 (2006) 25-32.
Fuat Topuz, et al., Magnesium ions and alginate do form hydrogels: a rheological study, Soft Matter, 2012, 8, 4877-4881.
Yrr A. Mørch, et al., Effect of Ca2+, Ba2+, and Sr2+ on Alginate Microbeads, Biomacromolecules 2006, 7, 1471-1480.
Huang, et al., "Kinetics and mechanisms of the conversion of silicate (45S5), borate and borosilicate glasses to hydroxyapatite in dilute phosphate solutions," J Mater Sci Mater Med 2006, 17: 583-596.
"An In-Vitro Comparison of Nano Hydroxyapatite, Novamin and Proargin Desensitizing Toothpastes—A SEM Study"; J Clin Diagn Res, 2016, 10(10): ZC51ZC54.
Cao Et La; "Methods for Biomimetic Remineralization of Human Dentine: A Systematic Review" ; Int. J. Mol. Sci. (2015) 16; pp. 4615-4627.
Copeland et al; "Microbeads: An Emerging Water Quality Issue" , Retrieved From fas.org, Jul. 20, 2015, 2 Pgs.
Coradin et al; "Silica-Alginate Composites for Microencapsulation" Applied Microbiology and Biotechnology, 61(5-6) pp. 429-434 (2003).
Davari, "Dentin Hypersensitivity: Etiology, Diagnosis and Treatment, A Literature Review," J Dent (Shiraz), 2013, 14(3): 136145).
Strassler et al; Dentinal Hypersensitivity: Etiology, Diagnosis and Management"; 9 Pages; Date Unknown; www.indeedce.com".
Fendall et al; "Contributing to Marine Pollution by Washing Your Face: Microplasitcs in Facial Cleansers" ; Marine Pollution Bulletin 58 (8): 12251228 (2009).
Forsback et al; "Mineralization of Dentin Induced by Treatment With Bioactive Glass S53P4 In Vitro" ; Acta Odontol Scand, 62 (2004); pp. 14-20.

Fu et al; "Bioactive Glass Innovations Through Academia-Industry Collaboration" ; International Journal of Applied Glass Science, 7 [2], (2016) pp. 139-146.
Fu et al; "Nature-Inspired Design of Strong, Tough Glass-Ceramics," MRS Bulletin, 2017, 42:220-225.
Graham, "High-Sensitivity Manetization Measurements" , J. Mater. Sci. Technol., vol. 16, No. 2, 2000, p. 97-101.
Gy, "Ion Exchange for Glass Strengthening," Mater Sci Ehg B, 2008, 149:159-165.
Han et al; "In Vivo Remineralization of Dentin Using an Agarose Hydrogel Biomimetic Mineralization System" ; Nature, Scientific Reports; (2017); 9 Pages.
Holand et al; "A Comparison of the Microstructure and Properties of the IPS EMPRESST2 and the IPS Empresst Glass-Ceramics" ; J Biomed Mater Res (Appl Biomater), 2000, 53: 297303.
Jacoby; "New Applications for Glass Emerge," Chem. Eng. News, 90 [25] 3436 (2012).
Jones; "Review of Bioactive Glass: From Hench to Hybrids" ; Acta Biomaterialia 9 (2013) pp. 4457-4486.
Kulal et al; "An In-Vitro Comparison of Nano Hydroxyapatite, Novamin and Proargin Desensitizing Toothpastes—A SEM Study" ; Journal of Clinical and Diagnostic Research; 2016; vol. 10 (10) ZC51-ZC54.
Kumaryadav et al; "Development of Zirconia Substituted 1393 Bioactive Glass for Orthopaedic Application" ; Oriental Journal of Chemistry; vol. 33, No. 6; (2017) pp. 2720-2730.
Lien et al; "Microstructural Evolution and Physical Behavior of a Lithium Disilicate Glass-Ceramic" ; Dent Mater 2015, 31: 928-940.
Low et al; "Reduction in Dental Hypersensitivity With Nano-Hydroxyapatite, Potassium Nitrate, Sodium Monoflurophosphate and Antioxidants" ; The Open Dentistry Journal; (2015), 9, pp. 92-97.
Marcolongo et al; "Surface Reaction Layer Formation In Vitro on a Bioactive Glass Fiber/Polymeric Composite" ; J. Biomed Mater. Res.; (1997); 37, pp. 440-448.
Miglani et al; "Dentin Hypersensitivity: Recent Trends in Management" ; J. Conserv. Dent. 2010; 13 (4) pp. 218-224.
Mintatoya et al; "Bioactive Glass Cloth That Propmotes New Bone Formation" ; Key Eng. Mater.; (2013) 529-530; pp. 266-269.
Ramanujan, Book Chapter 17, Magnetic Particles for Biomedical Applications, R. Narayan (ed.), Biomedical Materials, DOI 10.1007/978-0-387-84872-3 17, C Springer Science+Business Media, LLC 2009, pp. 477-491.
Sglavo; "Chemical Strengthening of Soda Lime Silicate Float Glass: Effect of Small Differences in the KNO3 Bath," Int J Appl Glass Sci, 2015, 6: 72-82.
Simhan; "Chemical Durability of ZrO2 Containing Glasses" ; Journal of Non-Crystalline Solids; 54 (1983) 335-343.
Singh et al; "Characterization of Si02—Na20—Fe203—Ca0—P205_B203 Glass Ceramics" ; Journal of Materials Science: Materials in Medicine, 10(8) pp. 481-484. (1999).
Succaria et al; "Prescribing a Dental Ceramic Material: Zirconia vs Lithium-Disilicate" ; The Saudi Dent J, 2011, 23: 165-166.
Wallenberger et al; "The Liquidus Temperature; Its Critical Role in Glass Manufacturing" ; International Journal of Applied Glass Science 1 [2] (2010) pp. 151-163.
Yao et al; "In Virto Bioactive Characteristics of Borate-Based Glasses With Controllable Degradation Behavior" ; J. Am. Ceram. Soc.; 90 [1]; 303-306 (2007).
Yin et al; "Effect of ZrO2 on the Bioactivity Properties of Gel-Derived CaO—P2O5—SiO2—SrO Glasses" ; Ceramics International; 43 (2017) pp. 9691-9698.
Yue et al; "Fiber Spinnability of Glass Melts" ; International Journal of Applied Glass Science; (2016) pp. 1-11.
Zhang et al; "Chipping Resistance of Graded Zirconia Ceramics for Dental Crowns" ; J Dent Res, 2012, 91:311315.
Neel et al; "Effect of Iron on the Surface, Degradation and Ion Release Properties of Phosphate Based Glass Fibres." Acta Biomaterialia 1, No. 5 (2005): 553-563.
Abo-Naf et al; "In Vitro Bioactivity Evaluation, Mechanical Properties and Microstructural Characterization of Na2O—CaO—B2O3—P2O5 Glasses"; Spectrochimica Acta Part A: Molecular and Biomolecular Spectroscopy; 144 (2015) pp. 88-98.

(56) References Cited

OTHER PUBLICATIONS

Sharmikn et al; "Effect of Boron Additiona on the Thermal, Degradation, and Cytocompatibility Properties of Phosphate-Based Glasses"; Biomed Research Internaitonal; vol. 2013; Article ID 902427; 12 Pages.

Buchilin et al; "Crystallization-Controlled Pore Retention in Calcium-Phosphate Glassceramics From Powder Sintering of CaO—P2O5—B2O3—Al2O3—TiO2—ZrO2 Glass"; Journal of Non-Crystalline Solids; 373-374 (2013) pp. 42-50.

Zheng et al; "Characteristics and Biocompatibility of Na2O—K2O—CaO—MgO—SrO—B2O3—P2O5 Borophosphate Glass Fibers"; Journal of Non-Crystalline Solids; 358 (2012) 387-391.

"Azo Materials, ""Silicon Dioxide"", accessed from: ""https://www.azom.com/properties.aspx?ArticleI D=1114"", accessed on Feb. 19, 2019,pp. 1-4 (Year: 2019)".

Kaklamani et al; "Mechanical Properties of Alginate Hydrogels Manufactured Using External Gelation", J. MeECH Beh. Biomed. Mater., 2014, pp. 135-142 (Year: 2014).

Maestrelli et al; "Development of Enteric-Coated Calcium Pectinate Microspheres Intended for Colonic Drug Delivery", Eur. J. Pharm. and Biopharm., 2008, pp. 508-518 (Year: 2008).

Mohini et al; "Studies on Influence of Aluminium Ions on the Bioactivity of B2O3—SiO2—P2O5—Na2O—CaO Glass System by Means of Spectroscopic Studies" ; Applied Surface Science; 287 (2013) pp. 46-53.

Noris-Suarez et al; "Osteoblastic Cells Biomineralized on Bioactive Glass and Glass-Ceramics of the SiO2Na20.CaO.K2O.MgO.P2O5 System Modified With Al2O3 and B2O3" ; Journal of Ceramic Processing Research; vol. 11, No. 2 (2010) pp. 129-137.

Pires et al; "The Role of Alumina in Aluminoborosilicate Glasses for Use in Glass-Ionomer Cements"; J. Mater. Chem, 19 (2009) pp. 3652-3660.

Gorustovich et al. "Osteoconductivity of strontium-doped bioactive glass particles: A histomorphometric study in rats," J Biomed Materials Res. Part A (2010) 92A: pp. 232-237.

Harianawala et al. "Biocompatibility of Zirconia" , J Adv Med Deni Sci Res 4(3) 2016, pp. 35-39.

Gunter et al. "Calcium pectinate gel beads obtained from callus cultures pectins aspromising systems for colon-targeted drug delivery," Carbohydrate Polymers, 2016, pp. 490-499.

Ogonczyk et al. "Microfluidic formulation of pectin microbeads for encapsulation and controlled release of nanoparticles," Biomicrofluidics, 2011, pp. 1-12.

\* cited by examiner

BIOACTIVE GLASS MICROSPHERES

This application claims the benefit of priority under 35 U.S.C. § 119 of U.S. Provisional Application Ser. No. 62/342,411 filed on May 27, 2016 the content of which is relied upon and incorporated herein by reference in its entirety.

CROSS-REFERENCE TO RELATED APPLICATIONS

The present application is related commonly owned and assigned U.S. Provisional Application Ser. Nos., filed concurrently herewith:

62/342,384, entitled "BIOACTIVE ALUMINOBORATE GLASSES";

62/342,377, entitled "MAGNETIZABLE GLASS CERAMIC COMPOSITION AND METHODS THEREOF";

62/342,381, entitled "LITHIUM DISILICATE GLASS-CERAMIC COMPOSITIONS AND METHODS THEREOF";

62/342,391, entitled "BIODEGRADABLE MICRO-BEADS"; and

62/342,426, entitled "BIOACTIVE BOROPHOSPHATE GLASSES," but does not claim priority thereto.

The present application is also related to commonly owned and assigned U.S. Application Ser. No. 62/189,880, filed Jul. 7, 2015, entitled "ANTIMICROBIAL PHASE-SEPARATING GLASS AND GLASS CERAMIC ARTICLES AND LAMINATES," which mentions a copper containing laminate having a degradable phase, which phase liberates cooper ion, and a non-degradable phase.

The entire disclosure of each publication or patent document mentioned herein is incorporated by reference.

BACKGROUND

The disclosure relates to bioactive glass compositions, bioactive glass microspheres made from the bioactive glass compositions, and to methods of making and using the compositions and the microspheres.

SUMMARY

In embodiments, the disclosure provides:
an aluminoborate composition;
an aluminoborosilicate glass composition;
a microsphere article comprised of the disclosed aluminoborate composition, a microsphere article comprised of the disclosed aluminoborosilicate glass composition, or a microsphere article comprised of a combination or mixture of the disclosed aluminoborate and aluminoborosilicate glass composition;
a method of making high-quality glass microspheres using the disclosed aluminoborate composition, the disclosed aluminoborosilicate glass composition, or a combination or mixture thereof;
a bioactive aluminoborate glass composition, a bioactive aluminoborosilicate glass composition, or a combination or mixture thereof, having excellent biocompatibility; and
a method of making and using each of the disclosed compositions.

The disclosed glass compositions, when used in bioactive applications, have shown excellent biocompatibility properties, and an ability to support of facilitate wound healing. Both solid and hollow microspheres can be prepared using, for example, a flame forming technique and the disclosed source compositions.

BRIEF DESCRIPTION OF THE DRAWINGS

In embodiments of the disclosure.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

In embodiments, the disclosed compositions, articles, methods of making, and methods of using provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

Definitions

"Glass," "glasses," or like terms can refer to a glass or a glass-ceramic.

"Glass article," or like terms can refer to any object made wholly or partly of a disclosed glass or a glass-ceramic.

"Particle," "microparticle," "bead," "microbead," "hollow bead," "hollow microbead," "hollow microparticle," "glass particle," "glass microparticle," or like terms refer to, for example, solid or hollow microspheres having diameter, for example, from 1 to 1000 microns, a hollow microsphere density of from 0.1 to 1.5 $g/cm^3$, a solid microsphere density of from 0.1 to 2.5 $g/cm^3$, and a particle aspect ratio, for example, from 5:1 to 1:5.

"Bioactivity Index" "index of bioactivity," "$I_B$," or like terms or symbols refer to, for example, the time for more than 50% of an interface of a specific bioactive material to be bonded by a biological material such as bone, tissue, and like materials. Mathematically, a bioactivity index (according to Hench; see Cao, W. et al., Bioactive Materials, Ceramics International, 22 (1996) 493-507.)) is, $I_B=100/t_{0.5bb}$, where $t_{0.5bb}$ is the time for more than 50% of a bioactive material's interface, such as an implant, to be bonded by a biological material such as bone, tissue, and like materials, including osteoproductive (Class A having both intracellular and extracellular responses, e.g., 45S5 Bioglass®) and osteoconductive (Class B extracellular response only at interface, e.g., synthetic hydroxyapatite) materials.

Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

Plastic microbeads and other ingredients have been used in personal care and cosmetics products for over 50 years. They are generally inexpensive, lightweight, strong, durable, and corrosion-resistant. They have been applied in a variety of leave-on and rinse-off formulations such as: deodorant, shampoo, conditioner, shower gel, lipstick, hair coloring, shaving cream, sunscreen, insect repellent, anti-wrinkle creams, moisturizers, hair spray, facial masks, baby care products, eye shadow, mascara, and like formulations. They serve many purposes such as a sorbent phase for delivery of active ingredients, film formation, exfoliation, viscosity regulation, and others. Both synthetic and natural polymers have been used to produce microbeads, including for example: polyethylene, polystyrene, polypropylene, polymethyl methacrylate, polyurethane, polyamide etc. Most of the plastic microbeads are non-degradable, for example, taking hundreds of years to completely degrade via an oxidative or photo-degradation route. Even biodegradable plastics, such as polylactic acid, will not degrade unless subjected to high temperatures. Furthermore, microbeads are designed to be discarded down the drain, and they have been reported in every major open ocean and many freshwater lakes and rivers (see C. M. Rochman, et al., Scientific evidence supports a ban on microbeads. *Environ Sci & Tech*, 2015, 49: 10759-10761). Their small size (e.g., 1 to 1000 microns) also makes them bioavailable to thousands of species across nearly all tropic levels (see C. M. Roch, et al., supra.).

Due to the increasing concerns on the microplastic pollutions, many countries including US seek to ban the use of plastic microbeads, which ban could create expanded markets for glass and ceramic microspheres substitutes. Glass microspheres have found wide applications in medicine, consumer goods, and various industries (see J. Berthing, et al., Hollow microspheres. *Chem Eng Technol*, 2004, 27: 829-837). Porous spheres have been used as a microcarrier for drugs and growth factors in tissue engineering (see Fu, H., et al., Hollow hydroxyapatite microspheres as a device for controlled delivery of proteins. *J Mater Sci: Mater Med.*, 2011; 22:579-91). Hollow glass spheres can be used, for example, as a lightweight filler in composite materials, a vehicle for controlled release of pharmaceuticals and radioactive tracers, and a media for storage and release of hydrogen (see V. V. Budov, Hollow glass microspheres. Use, properties and technology (review article), *Glass Ceram*, 1994, 51: 230-235). Commercially available hollow microspheres are usually based on silica. There is a potential demand for glass spheres, both solid and hollow, having controllable biodegradation and excellent biocompatibility, for example, in personal care and cosmetic products (see Napper, I. E., et al., Characterisation, quantity and sorptive properties of microplastics extracted from cosmetics. *Marine Pollution Bulletin* 99 (2015) 178-185.)

U.S. Pat. No. 7,709,027, entitled "Antimicrobial, anti-inflammatory, wound-healing glass powder and use thereof," to Schott, mentions a product for the treatment of skin irritations, acute and chronic wounds, comprising: a glass powder, whereby the glass of the glass powder comprises the following components in wt % on an oxide basis: 20-48% $SiO_2$, 0-40% $Na_2O$, 0-40% $K_2O$, 0-40% $Li_2O$, 0-40% CaO, 0-40% MgO, 0-8% $Al_2O_3$, 0% $P_2O_5$, 0-40% $B_2O_3$, 0-10% ZnO, whereby the total $Na_2O+K_2O+Li_2O+CaO+MgO$ amounts to 15 to 80%, the amount of Pb is less than 20 ppm, the glass of the glass powder is free from Ag, and the average size of the glass particles of the glass powder is less than 20 microns.

U.S. Pat. No. 7,166,549, entitled "Antimicrobial, Anti-Inflammatory, Wound-Healing And Disinfecting Glass And Use Thereof;" to Schott, mentions an antimicrobial, anti-inflammatory and disinfecting glass, whereby the glass comprises in wt %: 30-95% $SiO_2$, 0-40% $Na_2O$, 0-40% $K_2O$, 0-40% $Li_2O$, 0-35% CaO, 0-10% MgO, 0-10% $Al_2O_3$, 0-15% $P_2O_5$, % $B_2O_3$, 0-10% NaF, 0-10% LiF, 0-10% KF, 0-10% $CaF_2$, 0-5% $Ag_2O$, 0-10% $MgF_2$, 0-2% $Fe_2O_3$, and 0-10% $XJ_y$, where X is Li, Na, K, Rb, Cs, Be, Mg, Ca, Sr, Ba, Ag or Zn and y is 1 or y is 2 and the sum of $XJ_y >$ is 10 ppm.

In embodiments, the disclosure provides a group of alumino-borate and alumino-borosilicate glass compositions that exhibit excellent biocompatibility and can be formed into both solid and hollow microspheres.

Aluminoborate Glasses

In embodiments, the aluminoborate glass composition can comprise a source of, for example:

30 to 65% $B_2O_3$,
1 to 30% $Al_2O_3$,
1 to 5% $P_2O_5$,
3 to 30% $Na_2O$, and
5 to 30% CaO, based on a 100 mol % total of the composition.

In embodiments, the aluminoborate glass composition can further comprise a source of, for example:
0.1 to 15% $K_2O$,
0.1 to 15% MgO,
0.1 to 10% SrO, and
0.1 to 5% $SO_3$, based on a 100 mol % total of the composition.

In embodiments, a more preferred composition can include a source of, for example:
50 to 60% $B_2O_3$,
2 to 10% $Al_2O_3$,
1 to 3% $P_2O_5$,
4 to 10% $Na_2O$,
6 to 10% $K_2O$,
6 to 10% MgO, and
20 to 30% CaO, based on a 100 mol % total of the composition.

In embodiments, a most preferred composition can include a source of, for example:
50 to 60% $B_2O_3$,
5 to 10% $Al_2O_3$,
1 to 3% $P_2O_5$,
4 to 8% $Na_2O$,
6 to 10% $K_2O$,
6 to 10% MgO,
20 to 24% CaO, and
0.2 to 2% $SO_3$, based on a 100 mol % total of the composition.

Aluminoborosilicate Glasses

In embodiments, the disclosed aluminoborosilicate glass composition can comprise a source of, for example:
50 to 60% ($B_2O_3$+$SiO_2$),
0.1 to 25% $SiO_2$,
25 to 59.9% $B_2O_3$,
2 to 10% $Al_2O_3$,
1 to 3% $P_2O_5$,
4 to 10% $Na_2O$,
6 to 10% $K_2O$,
6 to 10% MgO, and
20 to 30% CaO, based on a 100 mol % total of the composition.

In embodiments, the aluminoborosilicate glass composition can further comprise a source of $SO_3$ from 0.2 to 2 mol % $SO_3$, based on a 100 mol % total of the composition.

In embodiments, a more preferred glass composition can comprise a source of, for example:
50 to 60% ($B_2O_3$+$SiO_2$),
4 to 25% $SiO_2$,
25 to 56% $B_2O_3$,
2 to 10% $Al_2O_3$,
1 to 3% $P_2O_5$,
4 to 8% $Na_2O$,
6 to 10% $K_2O$,
6 to 10% MgO,
20 to 24% CaO, and
0.2 to 2% $SO_3$, based on a 100 mol % total of the composition.

In embodiments, the disclosed aluminoborate or aluminoborosilicate glass composition can further comprise, for example, a form factor selected from a hollow microsphere, a solid microsphere, or a combination or mixture thereof, that is, where the glass composition has a particle shape, such as a sphere, egg-shape, or like geometry.

In embodiments, the form factor can have, for example, associated therewith a pharmaceutical, a nutri-ceutical, and like functional materials or vehicles, or a combination thereof.

In embodiments, the hollow microsphere, the solid microsphere, or a combination thereof, can have, for example, a diameter of from 1 to 1000 microns.

In embodiments, the hollow microsphere can have a density, for example, of from 0.1 to 1.5 g/cm$^3$.

In embodiments, the hollow microsphere can be a carrier, for example, for a therapeutic agent, and like functional ingredients.

In embodiments, the therapeutic agent can be, for example, a pharmaceutical, a biologic, or a mixture thereof, e.g., anti-biotic for the controlled release treatment of, for example, chronic infection; an anti-viral for the controlled release treatment of, for example, a virus; an anti-cancer agent for the controlled release treatment of a carcinoma.

In embodiments, the disclosure provides a wound healing composition, comprising, for example:
an aqueous extract of a composition selected from at least one of:
  an aluminoborate composition comprising:
    30 to 65% $B_2O_3$,
    1 to 30% $Al_2O_3$,
    1 to 5% $P_2O_5$,
    3 to 30% $Na_2O$, and
    5 to 30% CaO, based on a 100 mol % total of the composition;
  an aluminoborate composition comprising:
    30 to 65% $B_2O_3$,
    1 to 30% $Al_2O_3$,
    1 to 5% $P_2O_5$,
    3 to 30% $Na_2O$,
    5 to 30% CaO,
    0.1 to 15% $K_2O$,
    0.1 to 15% MgO,
    0.1 to 10% SrO, and
    0.1 to 5% $SO_3$, based on a 100 mol % total of the composition;
  an aluminoborosilicate composition comprising:
    50 to 60% ($B_2O_3$+$SiO_2$),
    0.1 to 25% $SiO_2$,
    25 to 59.9% $B_2O_3$,
    2 to 10% $Al_2O_3$,
    1 to 3% $P_2O_5$,
    4 to 10% $Na_2O$,
    6 to 10% $K_2O$,
    6 to 10% MgO, and
    20 to 30% CaO, based on a 100 mol % total of the composition; or a combination thereof.

In embodiments, the liquid portion of the aqueous extract, prior to extraction, comprised a DMEM medium supplemented with 4.5 g/L glucose, 2 mM L-glutamine, and 10% fetal bovine serum.

In embodiments, the wound healing composition can further comprise, for example, an article including the composition, for example, a liquid vehicle or solid support, a wound dressing, a bandage, an ointment, a salve for oral or topical application, a dosage form for oral or topical administration, such as for healing wounds or cells in the mouth or gastrointestinal tract.

In embodiments, the disclosure provides a method of wound healing, comprising:
contacting wound cells and the abovementioned wound healing composition for a time sufficient to heal, such as from 1 min to 90 days, one or more of the wound cells.

In embodiments, the disclosed compositions and methods thereof are advantaged in several aspects, including for example:

solid glass microspheres, hollow glass microspheres, or mixtures thereof, can be produced from the disclosed glass compositions and methods;

the disclosed compositions can support in vitro wound healing and angiogenesis;

the disclosed compositions have applications in cosmetic, soft tissue regeneration, and other healthcare applications; and the disclosed compositions can provide a more environmentally friendly and degradable material as an alternative to conventional polymer microspheres.

Representative examples of the disclosed aluminoborate compositions and the disclosed aluminoborosilicate compositions are listed in Table 1. Example C-1 is a comparative example, which is free of $Al_2O_3$.

TABLE 1

Examples of the disclosed aluminoborate compositions (Ex. C-2 to C-10) and aluminoborosilicate compositions (Ex. C-11 to C-15).

| Oxides (mol %) | C-1[1.] | C-2 | C-3 | C-4 | C-5 | C-6 | C-7 | C-8 |
|---|---|---|---|---|---|---|---|---|
| $B_2O_3$ | 54.6 | 50.5 | 48.8 | 38.6 | 34.6 | 50.4 | 50.3 | 50.1 |
| $SiO_2$ | 0.0 | 0.0 | 0.0 | 0.0 | 0.0 | 0.0 | 0.0 | 0.0 |
| $Al_2O_3$ | 0.0 | 7.4 | 10.7 | 16.0 | 20.0 | 7.4 | 7.4 | 7.3 |
| $P_2O_5$ | 1.7 | 1.6 | 1.5 | 1.7 | 1.7 | 1.6 | 1.6 | 1.6 |
| $Na_2O$ | 6.0 | 5.6 | 5.4 | 6.0 | 6.0 | 5.5 | 5.5 | 5.5 |
| $K_2O$ | 7.9 | 7.3 | 7.1 | 7.9 | 7.9 | 7.3 | 7.3 | 7.2 |
| MgO | 7.7 | 7.1 | 6.9 | 7.7 | 7.7 | 7.1 | 7.1 | 7.1 |
| CaO | 22.1 | 20.5 | 19.7 | 22.1 | 22.1 | 20.4 | 20.4 | 20.3 |
| $SO_3$ | 0.0 | 0.0 | 0.0 | 0.0 | 0.0 | 0.2 | 0.5 | 0.9 |

| Oxides (mol %) | C-9 | C-10 | C-11 | C-12 | C-13 | C-14 | C-15 |
|---|---|---|---|---|---|---|---|
| $B_2O_3$ | 49.6 | 50.3 | 45.7 | 41.1 | 36.6 | 32.0 | 27.4 |
| $SiO_2$ | 0.0 | 0.0 | 4.6 | 9.1 | 13.7 | 18.3 | 22.9 |
| $Al_2O_3$ | 7.3 | 7.3 | 7.3 | 7.3 | 7.3 | 7.3 | 7.3 |
| $P_2O_5$ | 1.5 | 1.6 | 1.6 | 1.6 | 1.6 | 1.6 | 1.6 |
| $Na_2O$ | 5.5 | 5.5 | 5.5 | 5.5 | 5.5 | 5.5 | 5.5 |
| $K_2O$ | 7.2 | 7.2 | 7.2 | 7.2 | 7.2 | 7.2 | 7.2 |
| MgO | 7.0 | 7.0 | 7.0 | 7.0 | 7.0 | 7.0 | 7.0 |
| CaO | 20.1 | 20.2 | 20.2 | 20.2 | 20.2 | 20.2 | 20.2 |
| $SO_3$ | 1.8 | 0.9 | 0.9 | 0.9 | 0.9 | 0.9 | 0.9 |

[1.]Example C-1 is a comparative example.

In embodiments, the disclosed compositions can be free of or substantially free of at least one of, for example, $Fe_2O_3$, ZnO, CuO, ZnO, and $TiO_2$, or any combination or mixtures thereof.

In embodiments, the disclosed glasses can typically be melted at a temperature below 1300° C., and in certain embodiments below 1200° C., making it possible to melt in a relatively small commercial glass tank. Microspheres can be produced using, for example, a flame forming technique with the disclosed compositions. Hollow spheres can be obtained in compositions containing a blowing agent (e.g., $SO_3$).

Methods for making glass microspheres are known, see for example, U.S. Pat. Nos. 3,323,888, and 6,514,892. Methods for making hollow glass microspheres include, for example, U.S. Pat. Nos. 2,978,339; 3,323,888; 5,14,892; and 6,254,981; and Campbell, J. H., et al., Preparation and Properties of Hollow Glass Microspheres for Use in Laser Fusion Experiments," Technical Report No. UCRL-53516, Lawrence Livermore National Lab., CA (USA), Nov. 1, 1983.

Figure 1:
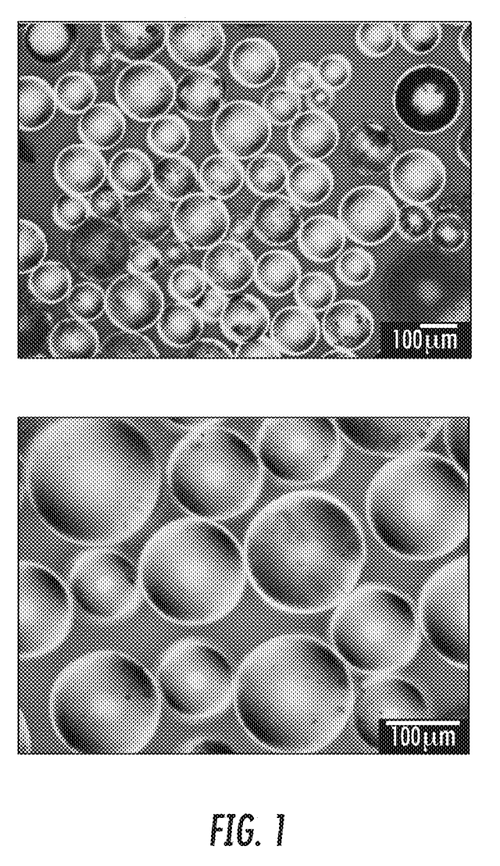
FIG. 1 shows solid microspheres at different magnifications that were prepared using a flame forming technique using example composition 2.

In embodiments, the glass compositions can be fashioned into solid microspheres (see FIG. 1).

In embodiments, glass microspheres can be prepared by, for example:

preparing a semi-product (frit) of at least one of the disclosed compositions, which semi-product consists of powders of defined chemical and granulometric compositions; and forming glass microspheres from the semi-product.

A sol-gel or a flame forming technique are widely used methods to produce glass microspheres. A sol-gel process generally includes the preparation of an aqueous solution of basic silicate containing additional special reagents (e.g., boric acid, urea, etc.), subsequent drying of the solution in a spray dryer, and fabrication of powders of defined granulometric composition, chemical treatment of the glass microspheres in acid solution to remove excess basic components, washing in water, and drying of the finished products (see V. V. Budov, supra.). In a flame forming process, glass microspheres are fabricated from previously synthesized glass powders. The glass frits are spheroidized by, for example, passing the frits through a flame of a gas-oxygen burner at a temperature of from 1000 to 1800° C., or through a vertical split furnace having a similar temperature range. The diameter of the spheres can be, for example, from 1 to 1000 microns, depending on the size of the glass frits. Fine frits (e.g., less than 100 microns) can be obtained using, for example, a jet mill, an attrition mill or ball mill; coarse particles can be produced by crushing glass using, for example, a steel mortar and pestle.

Figure 2:
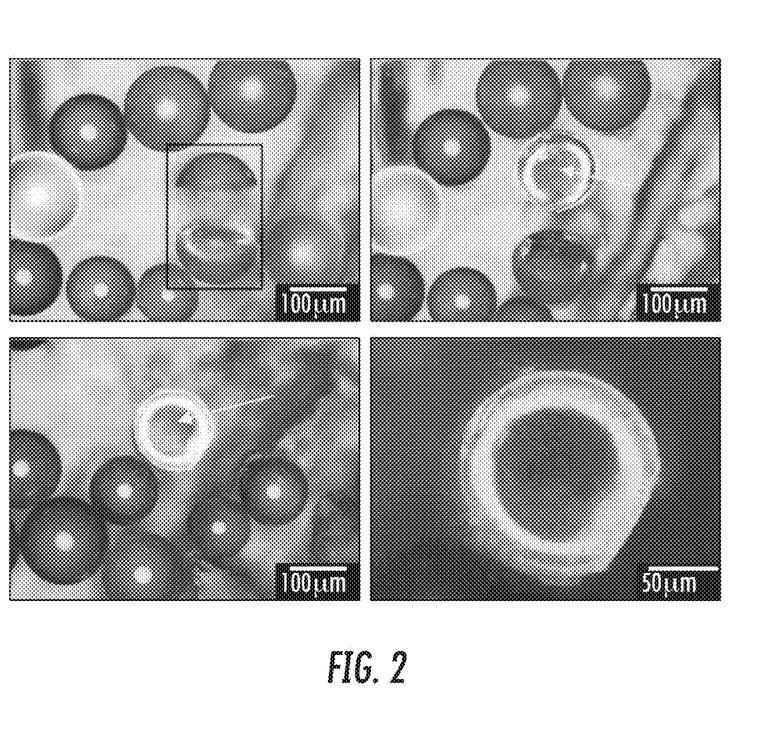
FIG. 2 shows examples of hollow glass microspheres that were prepared using a flame forming method using example composition 8.
Figure 3A:
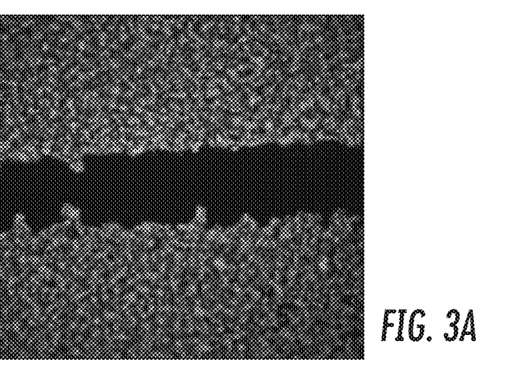
FIGS. 3A to 3D demonstrate wound healing accomplished with the comparative and disclosed compositions.
Figure 3B:
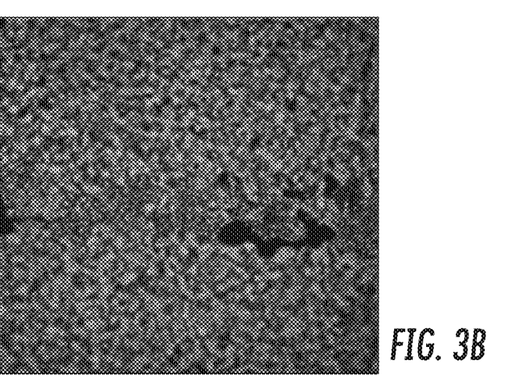
Figure 3C:
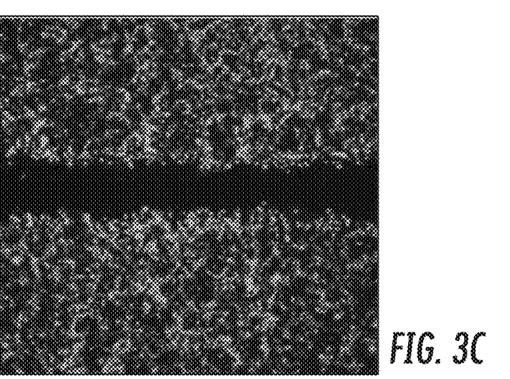
Figure 3D:
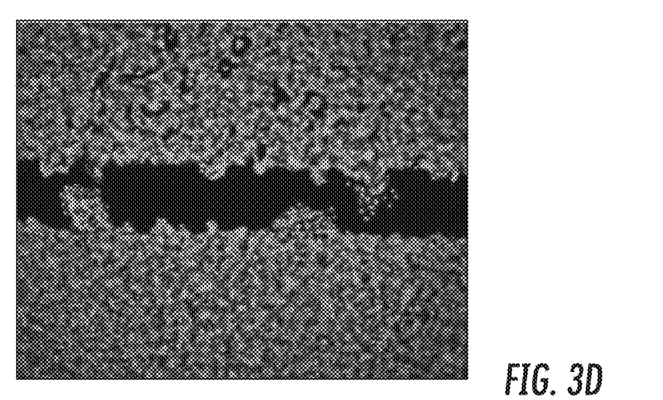

In embodiments, hollow glass microspheres can be produced by adding a blowing agent such as $SO_3$ into the glass batch compositions (FIG. 2). The blowing agent decomposes and releases gas to form a single hollow cavity at the center of the sphere during the spheroidizing process. The density of the hollow spheres can be determined by the concentration of the blowing agent included in the glass, and can vary, for example, from 0.1 to 1.5 $g/cm^3$. The hollow glass microspheres exhibit substantial advantages over plastics microbeads, for example: they are more environmentally friendly and more biodegradable; they can provide additional functions or benefits such as wound healing, and anti-oxidation; they have a higher refractive index, making them appealing for cosmetic and beauty enhancement products; they can produce a luxurious or lubricious tactile sensation on the skin; they can have a good oil absorption rate and can improve the compatibility between different ingredients; and the glass compositions can be easily modified to incorporate desired functions. FIG. 2 shows examples of hollow glass microspheres that were prepared using a flame forming method using example composition 8. A sample of the hollow microspheres was placed on a Scotch® tape ribbon and an individual microsphere was sectioned using a microtome to show the large internal spherical cavity within the center of the sectioned microsphere.

In embodiments, the physical, chemical, optical, and mechanical properties are mainly dependent on the glass compositions. For example, the density of the microspheres can be controlled by adding a different amount of blowing agent to control the shell thickness. The durability of the spheres can be manipulated by, for example, $B_2O_3/Al_2O_3$ swap or $B_2O_3/SiO_2$ in the glass compositions. The visual appearance or color of the spheres can be modified by, for example, doping the glasses with transition metals such as Au, Ag, Cu, Ni, Co, Fe, Mn, Cr, and V.

Figure 4:
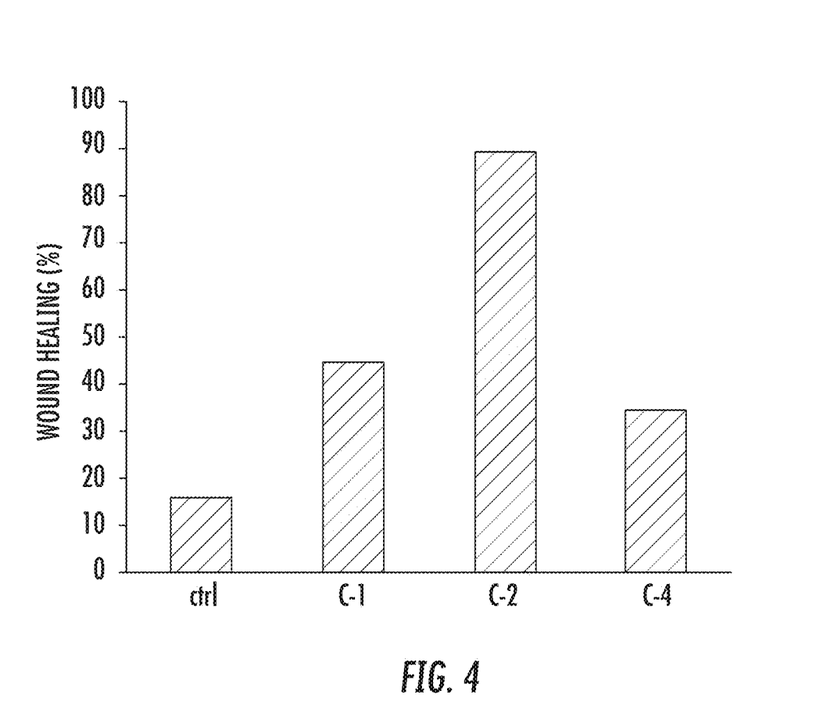
FIG. 4 shows the influence of the glass compositions comparative C-1, and disclosed compositions 2 and 3, on the percentage of wound healing.
Figure 5A:
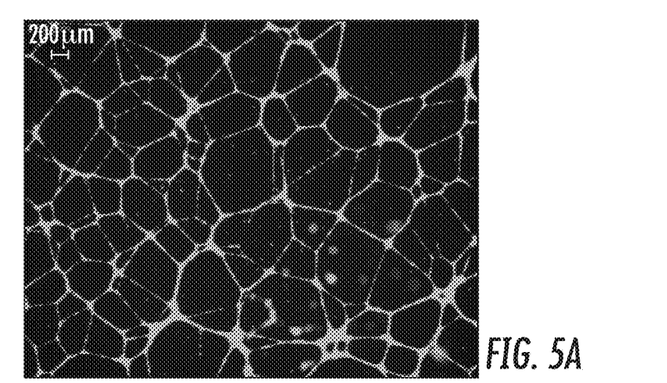
FIGS. 5A to 5D demonstrate examples of disclosed compositions that have excellent capability to support angiogenesis that is significant for wound healing, particularly for the $Al_2O_3$-containing borate glass compositions (Example 8).
Figure 5B:
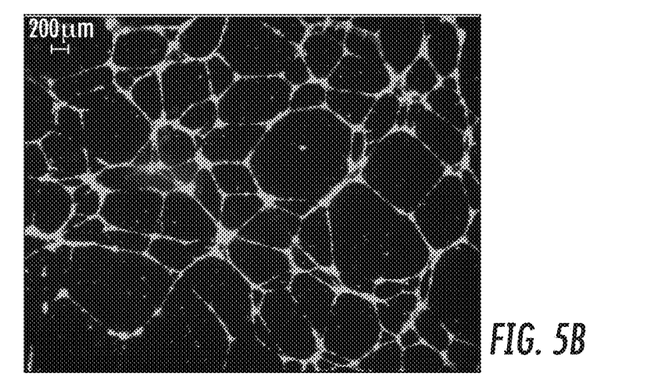
Figure 5C:
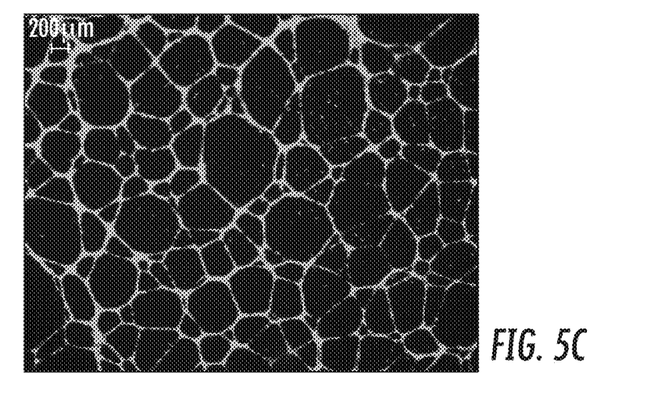
Figure 5D:
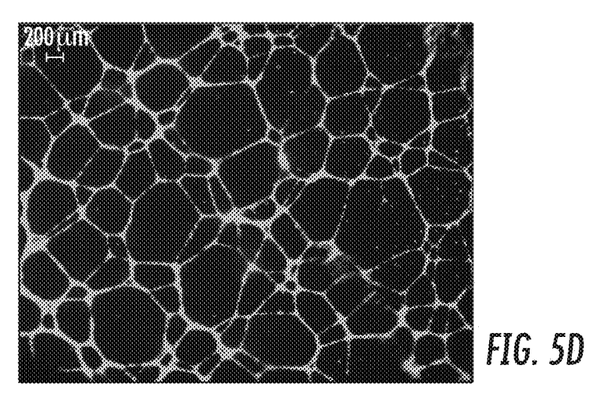

In embodiments, the disclosed compositions have been demonstrated to support improved in vitro wound healing (FIGS. 3 and 4). In particular, a faster gap healing occurred in Example Composition 2 (C-2) containing about 8 mol %

$Al_2O_3$, suggesting its application for skin repair, wound healing, tissue engineering, and cosmetic applications. Although not limited by theory, the release of ions, such as $Na_2O$ and CaO from the disclosed $Al_2O_3$-containing glass compositions, are believed to account for the observed improved in vitro bioactivity performance.

FIGS. 3A to 3D demonstrate wound healing accomplished with the comparative and disclosed compositions; specifically, Control medium without glass extract (3A); a medium containing an extract from Example 2 glass composition (C-2) (3B); a medium containing an extract from Comparative glass composition 1 (C-1) (3C); and a medium containing an extract from Example 3 glass composition (C-3) (3D). Glass extracts were obtained by soaking bioactive glass discs (12.5 mm in diameter×2 mm thick) from example compositions in a cell culture medium (DMEM medium supplemented with 4.5 g/L glucose, 2 mM L-glutamine, 10% fetal bovine serum) at 37° C., 5% $CO_2$ humid atmosphere for one week. The liquid extracts showed excellent capability to support wound healing, particularly for the $Al_2O_3$-containing borate glass compositions (e.g., Example glass composition 8; C-8). The CytoSelect™ 24-well Wound Healing Assay (Assay kit from Cell Biolabs, Inc.) was used to evaluate the capability of these glass extracts to support wound healing. The kit contains 2×24-well plates each containing twelve (12) proprietary treated plastic inserts, which create a wound field with a defined gap of 0.9 mm for measuring the migratory and proliferation rates of cells. HaCaT cells were added to the well with an insert in place. The insert was removed after a cell monolayer was formed to generate 0.9 mm wide "wound field." The cells were then cultured in medium or medium containing glass ionic extraction. The ionic extraction: the glass disc was subsequently added to the well with 2 mL of cell culture medium, incubated at 37° C. with 5% $CO_2$ in a humidified incubator for a week.

FIG. 4 shows the influence of the comparative example glass composition C-1, and disclosed compositions 2 and 3 (C-2 and C-3), on the percentage of wound healing. The example glass composition 2 shows a superior capability to support wound healing. The graph was based on an area analysis of wound healing shown in FIG. 3.

In embodiments, the disclosed compositions have been demonstrated to support angiogenesis (see FIG. 5), which is significant for wound healing. More cellular loops were found in a culture medium containing the example compositions compared to a control composition.

FIGS. 5A to 5D demonstrate examples of disclosed compositions that have excellent capability to support angiogenesis, particularly for the $Al_2O_3$-containing borate glass compositions (e.g., Example 8). Control (without a glass disc): 89 loops (5A); a glass disc of comparative composition 1 (C-1): 53 loops (5B); a glass disc of Example composition 2 (C-2): 109 loops (5C); and glass disc of Example composition 3 (C-3): 99 loops (5D).

Corning® Matrigel® was thawed at 4° C. the day before experiment. A glass disc mentioned above was added into the well of a 24-well microplate. The microplate was placed on wet ice, and the thawed Matrigel® was added on top of the glass disc. The microplate was then incubated at 37° C. for 30 min until gelled. Corning® HUVEC-2 cells were seeded and cultured for 16 to 18 hr. The tube formation was imaged and measured after labeling with Corning® Calcein AM fluorescent dye. HUVEC-2 culture medium: Lonza EBM™ Basal Medium with 2% fetal bovine serum, bovine brain extract, ascorbic acid, hydrocortisone, and epidermal growth factor.

In embodiments, the disclosed compositions in angiogenic applications have faster degradation and faster ion release in solution or in bioactive applications compared to a control composition.

In embodiments, the excellent biocompatibility of the disclosed compositions make them suitable for tissue engineering application. Porous glass scaffolds can be produced by sintering glass spheres into a 3-D construct for bone repair and regeneration.

The biocompatibility and degradation of the disclosed compositions are influenced by glass compositions. In the disclosed compositions, $B_2O_3$ serves as a primary glass-forming oxide. Borate glass is much less durable than silicate glass, making it attractive for fast degradation. However, at sufficiently high concentrations, boron is toxic. The most sensitive end point of boron toxicity appears to be chronic toxicity, including developmental and reproductive toxicity. In embodiments, limiting the toxicity arising from fast degradation and controlling the degradation rate of the disclosed compositions was achieved.

In embodiments, the disclosed aluminoborosilicate glass compositions having $SiO_2$ content can serve as another glass-forming oxide, can function to stabilize the networking structure of glass, and can improve the chemical durability of the compositions. However, the glasses can't contain too much $SiO_2$ since the melting temperature (200 poise temperature) of pure $SiO_2$ or high-$SiO_2$ glasses is undesirably high.

In embodiments, the $P_2O_5$ also serves as a network former. The liberation of phosphate ions from the surface of bioactive glasses contributes to the formation of apatite. Loading the disclosed bioactive glasses with releasable phosphate ions can increase the apatite formation rate and the binding capacity of the bone tissue. Additionally, $P_2O_5$ increases the melt viscosity of the glass, which in turn expands the range of operating temperatures, and is advantageous in glass manufacture.

In embodiments, the $Al_2O_3$ can also serve as a glass former in the disclosed glass compositions. A higher $Al_2O_3$ content generally increases the melt viscosity, and increases in $Al_2O_3$ relative to the alkalis or the alkaline earths generally results in improved durability. The structural role of the aluminum ions can depend upon the glass composition. However, $Al_2O_3$ is generally not present or minimized in silicate-based bioactive glasses of the prior art since it substantially decreases their bioactivity (see Hench, Bioceramics. *J AM Ceram Soc*, 1998, 81:1705-28).

In embodiments, the alkali oxides (i.e., $Li_2O$, $Na_2O$, $K_2O$, $Rb_2O$, and $Cs_2O$) serve as aids in achieving a low melting temperature and a low liquidus temperature. The addition of alkali oxides to glass compositions is known to improve bioactivity (Fu, H., et al., supra.).

In embodiments, divalent cation oxides (e.g., alkaline earth oxides) can also improve the melting behavior and the bioactivity of the glass. In a specific example, CaO dissolving from the disclosed glass compositions was able to react with a source of $P_2O_5$, for example, in the glass composition or from surrounding media to form apatite when the disclosed glass compositions were immersed in a simulated body fluid (SBF) or in vivo. The release of $Ca^{2+}$ ions from the surface of the disclosed glass compositions contributes to the formation of a layer rich in calcium phosphate.

In embodiments, a blowing agent, for example, source of $SO_3$, can be used to form hollow glass microspheres. At elevated temperatures the $SO_3$ decomposes into $SO_2$ and $O_2$ and can produce a large cavity within the glass microspheres.

Wound Healing Articles and Wound Healing Methods

In embodiments, the disclosure provides a wound healing composition or article comprising, for example:
a glass composition selected from at least one of:
an aluminoborate composition comprising:
30 to 65% $B_2O_3$,
1 to 30% $Al_2O_3$,
1 to 5% $P_2O_5$,
3 to 30% $Na_2O$, and
5 to 30% CaO, based on a 100 mol % total of the composition;
an aluminoborate composition comprising:
30 to 65% $B_2O_3$,
1 to 30% $Al_2O_3$,
1 to 5% $P_2O_5$,
3 to 30% $Na_2O$,
5 to 30% CaO,
0.1 to 15% $K_2O$,
0.1 to 15% MgO,
0.1 to 10% SrO, and
0.1 to 5% $SO_3$, based on a 100 mol % total of the composition;
an aluminoborosilicate composition comprising:
50 to 60% ($B_2O_3$+$SiO_2$),
0.1 to 25% $SiO_2$,
25 to 59.9% $B_2O_3$,
2 to 10% $Al_2O_3$,
1 to 3% $P_2O_5$,
4 to 10% $Na_2O$,
6 to 10% $K_2O$,
6 to 10% MgO, and
20 to 30% CaO, based on a 100 mol % total of the composition;
or a combination thereof; and
a form factor selected from a hollow microsphere, a solid microsphere, or a combination thereof.

In embodiments, the wound healing article can further comprise, for example: a pharmaceutical (e.g., an antibiotic compound within a hollow microsphere for controlled release of antibiotics in chronic infection), a nutri-ceutical, or a combination thereof, associated with the form factor, for example, coated on the article surface, encapsulated within the hollow microsphere, and like combinations or formulations.

In embodiments, the wound healing article can further comprise at least one of, for example:
a solid support or carrier, e.g., a bandage, a patch, an implant, a stent, etc., that is coated or impregnated with the composition form factor; a gel; etc.;
a liquid carrier, e.g., a liquid dispersion medium, culture medium, etc.; and
optionally a formulation, preparation, or a delivery vehicle, or a combination thereof.

In embodiments, the disclosure provides a method of wound healing comprising, for example:
contacting wound cells and a disclosed wound healing article, e.g., combining a disclosed bioactive composition including at least one of the disclosed glass compositions and wound cells, such as in vitro, in vivo, in culture, and like live cell combinations, comprising a composition selected from at least one of:
an aluminoborate composition comprising:
30 to 65 mol % $B_2O_3$,
1 to 30 mol % $Al_2O_3$,
1 to 5 mol % $P_2O_5$,
3 to 30 mol % $Na_2O$, and
5 to 30 mol % CaO, based on a 100 mol % total of the composition;
an aluminoborate composition comprising:
30 to 65 mol % $B_2O_3$,
1 to 30 mol % $Al_2O_3$,
1 to 5 mol % $P_2O_5$,
3 to 30 mol % $Na_2O$,
5 to 30 mol % CaO,
0.1 to 15% $K_2O$,
0.1 to 15% MgO,
0.1 to 10% SrO, and
0.1 to 5% $SO_3$, based on a 100 mol % total of the composition;
an aluminoborosilicate composition comprising:
50 to 60% ($B_2O_3$+$SiO_2$),
0.1 to 25% $SiO_2$,
25 to 59.9% $B_2O_3$,
2 to 10% $Al_2O_3$,
1 to 3% $P_2O_5$,
4 to 10% $Na_2O$,
6 to 10% $K_2O$,
6 to 10% MgO, and
20 to 30% CaO, based on a 100 mol % total of the composition; or a combination thereof; and
the composition having a form factor selected from a hollow microsphere, a solid microsphere, or a combination thereof.

EXAMPLES

The following Examples demonstrate making, use, and analysis of the disclosed compositions and methods in accordance with the above general procedures.

Example 1

Method of Making an Aluminoborate Glass

Example Compositions 2 to 10 were melted in an electric furnace using batching materials including boric acid, alumina, sodium carbonate, potassium carbonate, limestone, magnesia, calcium phosphate and sodium sulfate. Prior to melting, the batches were vigorously mixed in a plastic jar using a Turbula® mixer. Then they were transferred to a platinum crucible with an internal volume of approximately 650 cc. The crucible was then loaded into an annealing furnace to calcine the batch at 250° C. for 24 hr. The calcined batches were melted at 1200° C. for 6 hr and then glass melt was poured on a steel plate, and annealed at 500° C.

Example 2

Method of Making a Solid Microsphere Aluminoborate Glass with the Glass of Example 1

Solid glass microspheres can be prepared from all of the disclosed example glass compositions of Table 1. The production of glass microspheres generally includes two stages: preparation of semi-product (frit), which consists of powders of defined chemical and granulometric compositions; and forming of glass microspheres. Sol-gel processing, flame-forming, vertical furnace, liquid droplet, rotating electrical arc, and argon plasma jet are common methods used to produce glass microspheres. In the flame forming process, glass cullets of the approximate desired particle sizes are first prepared by crushing the glass using a steel mortar and a pestle, then milling with, for example, jet milling, attrition milling, ball milling, or like methods. Additionally or alternatively, the crushed or milled particles can be spheroidized by passing the reduced particles through a flame of a gas-oxygen burner at a temperature of from 1000 to 1800° C., or through a vertical furnace at a similar temperature. Other common microsphere forming methods mentioned above can also be used. The diameter of the glass microspheres can be, for example, from 1 to 1000 micrometers, depending on the size of the glass frits.

Example 3

Method of Making a Hollow Microsphere Aluminoborate Glass with the Glass of Example 1

Hollow glass microspheres are produced by batching a blowing agent such as $SO_3$ into the glass compositions. The blowing agent thermally decomposes and releases gas to form a single hollow cavity at the center of the sphere during the spheroidizing process. Similar to the solid glass microspheres, the production of hollow glass microspheres also includes two stages: preparation of semi-product (frit), which consists of powders of defined chemical and granulometric compositions; and forming the glass microspheres. Glass cullet of desired particle sizes are first prepared by crushing glass using steel mortar and pestle, then milling, for example, jet milling, attrition milling, or ball milling. The milled particles can be spheroidized by passing the particles through a flame of gas-oxygen burner at a temperature of from 1000 to 1800° C. or through a vertical split furnace of a similar temperature range. The diameter of the glass microspheres can be from 1 to 1000 micrometers, depending on the size of the glass frits.

Example 4

Method of Wound Healing with the Solid Microsphere of Example 2

The ability of disclosed bioactive glasses to support wound healing can be evaluated using a CytoSelect™ 24-well Wound Healing Assay (CytoSelect™ 24-Well Wound Healing Assay kit, Cell Biolabs, Inc.). A culture medium consisting of a DMEM medium supplemented with 4.5 g/L glucose, 2 mM L-glutamine, 10% fetal bovine serum containing an aqueous extract of the glass was used for the evaluation. Glass discs (12.5 mm in diameter×2 mm thick) or microspheres (solid or hollow, 150 to 300 micrometers) are soaked in the DMEM supplemented cell culture medium at 37° C., 5% $CO_2$ humid atmosphere for one week. The wound healing assay contains 2×24-well plates each containing 12 proprietary treated plastic inserts, which creates a wound field with a defined gap of 0.9 mm for measuring the migratory and proliferation rates of cells. HaCaT cells were added into the well with a plastic insert. The insert was removed after a cell monolayer was formed to generate 0.9 mm "wound field". The cells were then cultured in medium or medium containing a glass ionic extract. The glass ionic extract was obtained by an ionic extraction procedure where the glass disc was added to the well with 2 mL of cell culture medium (DMEM medium supplemented with 4.5 g/L glucose, 2 mM L-glutamine, 10% fetal bovine serum), incubated at 37° C. with 5% $CO_2$ in a humidified incubator for a week. The percentage of closure (wound healing) was defined as:

Percent Closure (%)=Migrated Cell Surface Area/ Total Surface Area×100 where Migrated Cell Surface Area=length of cell migration (mm)×2×length, and Total Surface Area=0.9 mm×length (mm);

Method of Wound Healing with the Hollow Microsphere Aluminoborate Glass of Example 3 (Prophetic)

Example 4 is repeated with the exception that the hollow microsphere aluminoborate glass of Example 3 is selected as the starting material.

Example 5

Method of Making an Aluminoborosilicate Glass

Example Compositions 11 to 15 were melted in an electric furnace using batching materials including sand, boric acid, alumina, sodium carbonate, potassium carbonate, limestone, magnesia, calcium phosphate and sodium sulfate. Prior to melting, the batches were vigorously mixed in a plastic jar using a Turbula® mixer. Then they were transferred to a platinum crucible with an internal volume of approximately 650 cc. The crucible was then loaded into an annealing furnace to calcine the batch at 250° C. for 24 hr. The calcined bathes were melted at 1200° C. for 6 hr and then glass melt was poured on a steel plate, and annealed at 500° C.

Example 6

Method of Making a Solid Microsphere Aluminoborosilicate Glass with the Glass of Example 5

Example 2 is repeated with the exception that the aluminoborosilicate glass of Example 5 is selected as the starting material.

Example 7 (Prophetic)

Method of Making a Hollow Microsphere Aluminoborosilicate Glass with the Glass of Example 5

Example 3 is repeated with the exception that the aluminoborosilicate glass of Example 5 is selected as the starting material for making hollow microsphere aluminoborosilicate glass.

Example 8 (Prophetic)

Method of Wound Healing with the Hollow Microsphere Aluminoborate Glass of Example 7

Example 4 is repeated with the exception that the hollow microsphere aluminoborate glass of Example 7 is selected as the wound healing composition.

Comparative Example 9

Example 1 was repeated with the exception that the source ingredients excluded $Al_2O_3$ and $SiO_2$, to from the comparative composition C-1 in Table 1. Comparative composition C-1 (also called 1393 B3) in Table 1 is based on Dermafuse, which is a nanofiber made from 1393 B3 glass, from Mo-Sci Health Care that resembles a cotton candy-like material (see todayswoundclinic.com/articles/twc-news-update-1). A pre-clinical trial reportedly showed the product was 98 percent effective at accelerating healing for patients with deep wounds.

The disclosure has been described with reference to various specific embodiments and techniques. However, it should be understood that many variations and modifications are possible while remaining within the scope of the disclosure.

What is claimed is:

1. An aluminoborate glass composition, comprising:
   30 to 65 mol % $B_2O_3$,
   7.3 to 30 mol % $Al_2O_3$,
   1 to 5 mol % $P_2O_5$,
   3 to 30 mol % $Na_2O$, and
   5 to 30 mol % CaO, based on a 100 mol % total of the composition; wherein the composition is a hollow microsphere, a solid microsphere, or a combination thereof.

2. The aluminoborate glass composition of claim 1, further comprising:
   0.1 to 15 mol % $K_2O$,
   0.1 to 15 mol % MgO,
   0.1 to 10 mol % SrO, and
   0.1 to 5 mol % $SO_3$, based on a 100 mol % total of the composition.

3. The aluminoborate glass composition of claim 1 further comprising a pharmaceutical, a biologic, a nutri-ceutical, or a combination thereof, associated with the hollow microsphere, the solid microsphere, or the combination thereof.

4. The aluminoborate glass composition of claim 1 wherein the hollow microsphere, the solid microsphere, or the combination thereof, has a diameter of from 1 to 1000 microns.

5. The aluminoborate glass composition of claim 1 wherein the hollow microsphere has a density of from 0.1 to 1.5 g/cm$^3$.

6. An aluminoborosilicate glass composition, comprising:
   50 to 60% ($B_2O_3$+$SiO_2$),
   0.1 to 25 mol % $SiO_2$,
   25 to 59.9 mol % $B_2O_3$,
   7.3 to 30 mol % $Al_2O_3$,
   1 to 3 mol % $P_2O_5$,
   4 to 10 mol % $Na_2O$,
   6 to 10 mol % $K_2O$,
   6 to 10 mol % MgO, and
   20 to 30 mol % CaO, based on a 100 mol % total of the composition.

7. The aluminoborosilicate glass composition of claim 6 further comprising from 0.2 to 2 mol % $SO_3$, based on a 100 mol % total of the composition.

8. The aluminoborosilicate glass composition of claim 6, wherein the composition is a hollow microsphere, a solid microsphere, or a combination thereof.

9. The aluminoborate glass composition of claim 8 further comprising a pharmaceutical, a biologic, a nutri-ceutical, or a combination thereof, associated with the hollow microsphere, a solid microsphere, or the combination thereof.

10. The aluminoborate glass composition of claim 8, further comprising a therapeutic agent situated within the hollow microsphere.

11. The aluminoborosilicate glass composition of claim 10 wherein the therapeutic agent is selected from at least one of: a pharmaceutical, a biologic, a nutri-ceutical, or a mixture thereof.

12. A wound healing article comprising:
    a glass composition selected from at least one of:
       an aluminoborate composition comprising:
          30 to 65 mol % $B_2O_3$,
          7.3 to 30 mol % $Al_2O_3$,
          1 to 5 mol % $P_2O_5$,
          3 to 30 mol % $Na_2O$,
          5 to 30 mol % CaO, and based on a 100 mol % total of the composition;
       an aluminoborate composition comprising:
          30 to 65 mol % $B_2O_3$,
          7.3 to 30 mol % $Al_2O_3$,
          1 to 5 mol % $P_2O_5$,
          3 to 30 mol % $Na_2O$,
          5 to 30 mol % CaO,
          0.1 to 15 mol % $K_2O$,
          0.1 to 15 mol % MgO,
          0.1 to 10 mol % SrO, and
          0.1 to 5 mol % $SO_3$, based on a 100 mol % total of the composition;
       an aluminoborosilicate composition comprising:
          50 to 60 mol % ($B_2O_3$+$SiO_2$),
          0.1 to 25 mol % $SiO_2$,
          25 to 59.9 mol % $B_2O_3$,
          7.3 to 30 mol % $Al_2O_3$,
          1 to 3 mol % $P_2O_5$,
          4 to 10 mol % $Na_2O$,
          6 to 10 mol % $K_2O$,
          6 to 10 mol % MgO, and
          20 to 30 mol % CaO, based on a 100 mol % total of the composition;
       or a combination thereof;
    wherein the is a hollow microsphere, a solid microsphere, or a combination thereof.

13. The wound healing article of claim 12 further comprising a pharmaceutical, a biologic, a nutri-ceutical, or a combination thereof, associated with the hollow microsphere, a solid microsphere, or the combination thereof.

14. The wound healing article of claim 12 further comprising at least one of:
    a solid support;
    a liquid carrier;
    or a combination thereof.

15. A method of wound healing, comprising:
    contacting wound cells with a wound healing article comprising a composition selected from at least one of:
    an aluminoborate composition comprising:
       30 to 65 mol % $B_2O_3$,
       7.3 to 30 mol % $Al_2O_3$,
       1 to 5 mol % $P_2O_5$,
       3 to 30 mol % $Na_2O$, and
       5 to 30 mol % CaO, based on a 100 mol % total of the composition;
    an aluminoborate composition comprising:
       30 to 65 mol % $B_2O_3$,
       7.3 to 30 mol % $Al_2O_3$,
       1 to 5 mol % $P_2O_5$,
       3 to 30 mol % $Na_2O$,
       5 to 30 mol % CaO,
       0.1 to 15 mol % $K_2O$,
       0.1 to 15 mol % MgO,
       0.1 to 10 mol % SrO, and
       0.1 to 5 mol % $SO_3$, based on a 100 mol % total of the composition;
    an aluminoborosilicate composition comprising:
       50 to 60 mol % ($B_2O_3$+$SiO_2$),
       0.1 to 25 mol % $SiO_2$,
       25 to 59.9 mol % $B_2O_3$,
       7.3 to 30 mol % $Al_2O_3$,
       1 to 3 mol % $P_2O_5$,
       4 to 10 mol % $Na_2O$,
       6 to 10 mol % $K_2O$,
       6 to 10 mol % MgO, and
       20 to 30 mol % CaO, based on a 100 mol % total of the composition;
    or a combination thereof;
    wherein the composition is a hollow microsphere, a solid microsphere, or a combination thereof.

16. A wound healing composition, comprising:
an aqueous extract of a composition selected from at least one of:
an aluminoborate composition comprising:
- 30 to 65 mol % $B_2O_3$,
- 7.3 to 30 mol % $Al_2O_3$,
- 1 to 5 mol % $P_2O_5$,
- 3 to 30 mol % $Na_2O$, and
- 5 to 30 mol % CaO, based on a 100 mol % total of the composition;

an aluminoborate composition comprising:
- 30 to 65 mol % $B_2O_3$,
- 7.3 to 30 mol % $Al_2O_3$,
- 1 to 5 mol % $P_2O_5$,
- 3 to 30 mol % $Na_2O$,
- 5 to 30 mol % CaO,
- 0.1 to 15 mol % $K_2O$,
- 0.1 to 15 mol % MgO,
- 0.1 to 10 mol % SrO, and
- 0.1 to 5 mol % $SO_3$, based on a 100 mol % total of the composition;

an aluminoborosilicate composition comprising:
- 50 to 60 mol % ($B_2O_3$+$SiO_2$),
- 0.1 to 25 mol % $SiO_2$,
- 25 to 59.9 mol % $B_2O_3$,
- 7.3 to 30 mol % $Al_2O_3$,
- 1 to 3 mol % $P_2O_5$,
- 4 to 10 mol % $Na_2O$,
- 6 to 10 mol % $K_2O$,
- 6 to 10 mol % MgO, and
- 20 to 30 mol % CaO, based on a 100 mol % total of the composition;

or a combination thereof.

17. The wound healing composition of claim 16, wherein the liquid portion of the aqueous extract, prior to extraction, comprises a culture medium consisting of a DMEM medium supplemented with 4.5 g/L glucose, 2 mM L-glutamine, and 10% fetal bovine serum.

18. The wound healing composition of claim 16, further comprising an article including the composition.

19. A method of wound healing, comprising:
contacting one or more wound cells and the wound healing composition of claim 16 for a time sufficient to heal one or more of the wound cells.

* * * * *

UNITED STATES PATENT AND TRADEMARK OFFICE
CERTIFICATE OF CORRECTION

PATENT NO. : 10,751,367 B2
APPLICATION NO. : 15/603208
DATED : August 25, 2020
INVENTOR(S) : Huayun Deng et al.

It is certified that error appears in the above-identified patent and that said Letters Patent is hereby corrected as shown below:

On the Title Page

In Column 2, item (57), Abstract, Line 1, delete "alumino-borosilicate" and insert -- aluminoborosilicate --, therefor.

On page 2, in Column 2, item (56), Foreign Patent Documents, Line 5 (approx.), delete "20130112422" and insert -- 20130112433 --, therefor.

On page 2, in Column 2, item (56), Other Publications, Line 33 (approx.), delete "baed" and insert -- based --, therefor.

On page 2, in Column 2, item (56), Other Publications, Line 34 (approx.), delete "Sciemce:" and insert -- Science: --, therefor.

On page 3, in Column 1, item (56), Other Publications, Line 63 (approx.), delete "Microplasitcs" and insert -- Microplastics --, therefor.

On page 3, in Column 2, item (56), Other Publications, Line 6, delete "Manetization" and insert -- Magnetization --, therefor.

On page 3, in Column 2, item (56), Other Publications, Line 38 (approx.), delete "Propmotes" and insert -- Promotes --, therefor.

On page 4, in Column 1, item (56), Other Publications, Line 1 (approx.), delete "Additiona" and insert -- Additional --, therefor.

On page 4, in Column 1, item (56), Other Publications, Line 3 (approx.), delete "Internaitonal" and insert -- International --, therefor.

On page 4, in Column 2, item (56), Other Publications, Line 18 (approx.), delete "aspromising"

Signed and Sealed this
Eleventh Day of October, 2022

Katherine Kelly Vidal
*Director of the United States Patent and Trademark Office*

CERTIFICATE OF CORRECTION (continued)
U.S. Pat. No. 10,751,367 B2 and insert -- as promising --, therefor.

In the Claims

In Column 15, Line 48, Claim 9, delete "aluminoborate" and insert -- aluminoborosilicate --, therefor.

In Column 15, Line 52, Claim 10, delete "aluminoborate" and insert -- aluminoborosilicate --, therefor.

In Column 16, Line 23, Claim 12, after "wherein the" insert -- composition --.